United States Patent
Krich et al.

(10) Patent No.: US 6,787,654 B2
(45) Date of Patent: Sep. 7, 2004

(54) METHOD FOR PRODUCING 2-CHLORO-5-CHLOROMETHYL-1,3-THIAZOLE

(75) Inventors: Sylvia Krich, Altenberg (AT); Christian Burger, Leonding (AT); Johann Altreiter, Neumarkt (AT); Birgit Zwölfer, Timelkam (AT)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/296,488
(22) PCT Filed: Apr. 26, 2001
(86) PCT No.: PCT/EP01/04693
§ 371 (c)(1), (2), (4) Date: Mar. 27, 2003
(87) PCT Pub. No.: WO01/90089
PCT Pub. Date: Nov. 29, 2001

(65) Prior Publication Data
US 2003/0153767 A1 Aug. 14, 2003

(30) Foreign Application Priority Data
May 23, 2000 (AT) .......................................... A895/2000

(51) Int. Cl.$^7$ ............................................. C07D 277/32
(52) U.S. Cl. ....................................................... 548/202
(58) Field of Search ......................................... 548/202

(56) References Cited

U.S. PATENT DOCUMENTS 4,748,243 A * 5/1988 Beck et al. .................. 548/202
5,811,555 A * 9/1998 Wakasugi et al. ........... 548/202

FOREIGN PATENT DOCUMENTS

EP 0 260 560 A 3/1988

* cited by examiner

*Primary Examiner*—Laura L. Stockton
(74) *Attorney, Agent, or Firm*—Rose M. Allen

(57) ABSTRACT

A process for the preparation of 2-chloro-5-chloromethyl-1,3-thiazole, in which allyl isothiocyanate of formula $CH_2=CH-CH_2-NCS$ is reacted at from −40° C. to +30° C., in a solvent that is inert under the reaction conditions, with from 1 to 2 mol of a chlorinating agent per mol of allyl isothiocyanate; to the reaction mixture so obtained there is added, at a reaction temperature of from 0° C. to the boiling temperature of the solvent used, from 1 to 5 mol of oxidising agent per mol of allyl isothiocyanate, and then 2-chloro-5-chloromethyl-1,3-thiazole is isolated from the reaction mixture and is optionally converted by crystallisation into high-purity 2-chloro-5-chloromethyl-1,3-thiazole.

9 Claims, No Drawings

METHOD FOR PRODUCING 2-CHLORO-5-CHLOROMETHYL-1,3-THIAZOLE

The invention relates to a process for the preparation of 2-chloro-5-chloromethyl-1,3-thiazole (CCT).

2-Chloro-5-chloromethyl-1,3-thiazole is a valuable intermediate in the preparation of pesticides or pharmaceutical products.

A large number of extremely varied processes for the preparation of CCT are already known from the literature.

For example, EP 0 260 560 and EP 0 446 913 describe the preparation of CCT by reaction of allyl isothiocyanate and of allyl isothiocyanate substituted by a leaving group, respectively, with a chlorinating agent, and EP 0 763 531 describes the reaction of 2-chloroallyl isothiocyanate with a chlorinating agent. Those processes have disadvantages, because, for example in the case of the first variant, a plurality of secondary products are formed so that the CCT prepared has a low degree of purity, and in the case of the second variant the starting material is obtainable only at high cost. Furthermore, a considerable excess of chlorinating agent must be used and the operation must be carried out at a high dilution. In addition, it is necessary to adhere exactly to the reaction temperature and the stable intermediate formed in the course of the reaction has to be converted into the desired end product exothermically in an additional reaction step. As an improvement EP 0 794 180 describes the preparation of CCT from 1,3-dichloropropene and a thiocyanate salt via 3-chloro-1-isothiocyanato-1-propene.

Other variants, for example the process according to EP 0 775 700, according to which CCT is prepared via 2-amino-5-methylthiazole by means of diazotisation and subsequent chlorination, likewise exhibit the disadvantage that CCT is contaminated by a large number of secondary products which can scarcely be removed or can be removed only with great difficulty and with high losses of yield.

The aim of the invention was to provide a new process that enables CCT to be prepared in high purity and high yield.

The invention accordingly relates to a process for the preparation of 2-chloro-5-chloromethyl-1,3-thiazole, wherein allyl isothiocyanate of formula $CH_2=CH-CH_2-NCS$ a) is reacted at from −40° C. to +30° C., in a solvent that is inert under the reaction conditions, with from 1 to 2 mol of a chlorinating agent per mol of allyl isothiocyanate and b) to the reaction mixture so obtained there is added, at a reaction temperature of from 0° C. to the boiling temperature of the solvent used, from 1 to 5 mol of oxidising agent per mol of allyl isothiocyanate and c) 2-chloro-5-chloromethyl-1,3-thiazole is isolated from the reaction mixture and d) is optionally converted by crystallisation into high-purity 2-chloro-5-chloromethyl-1,3-thiazole.

The starting compound used according to the invention for the preparation of CCT is allyl isothiocyanate of formula $CH_2=CH-CH_2-NCS$.

That compound is reacted in step a) with a chlorinating agent.

Chlorinating agents that come into consideration are chlorine and compounds from which chlorine is liberated under the reaction conditions. Examples of such compounds are sulfuryl chloride, $PCl_5$, $PCl_3$, $POCl_3$ etc.

The chlorinating agent is used according to the invention in an amount of from 1 to 2 mol per mol of allyl isothiocyanate. Preference is given to the use of from 1 to 1.6 mol and especially from 1 to 1.3 mol of chlorinating agent per mol of allyl isothiocyanate.

The reaction is carried out in a solvent that is inert under the reaction conditions. Suitable solvents are, for example, aliphatic or aromatic hydrocarbons, for example benzene, toluene, hexane, heptane, octane etc., halogenated aliphatic or aromatic hydrocarbons, for example dichloromethane, 1,2-dichloroethane, carbon tetrachloride, 1,1,2,2-tetrachloroethane, trichloromethane and trichloroethane, chlorobenzene, dichlorobenzenes, trichlorobenzene etc., ethers, for example diethyl ether, diisopropyl ether, tetrahydrofuran, dioxane, dimethoxyethane, etc., nitriles, for example acetonitrile, propionitrile, etc., amides, for example dimethylformamide, methylpyrrolidone, diethylformamide, etc., sulfoxides, for example dimethyl sulfoxide etc.

Preference is given to halogenated, aliphatic or aromatic solvents from the group dichloromethane, 1,2-dichloroethane, carbon tetrachloride, 1,1,2,2-tetrachloroethane, trichloromethane and trichloroethane, chlorobenzene and dichlorobenzenes.

The reaction temperature is from −40° C. to +30° C., preferably from −30° C. to +10° C. and especially from −20° C. to 0° C.

The reaction mixture is stirred at the appropriate reaction temperature for from a few minutes up to several hours. Stirring is preferably carried out for from about 5 minutes up to 5 hours and especially for from about 20 minutes up to 2 hours.

The reaction of allyl isothiocyanate and chlorinating agent yields an intermediate compound of formula

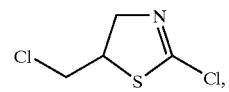

which is not, however, isolated from the reaction mixture.

The reaction mixture obtained by step a), which contains the above intermediate compound, is immediately after step a) subjected to the following reaction with oxidising agent (step b). For that purpose, in step b) either from 1 to 5 mol of oxidising agent per mol of allyl isothiocyanate are added to the reaction mixture. Suitable oxidising agents are, for example, peroxy acid, for example peracetic acid, m-chloroperbenzoic acid, acid/$H_2O_2$ mixtures, inorganic or organic peroxides, for example nickel peroxide, hydroperoxides or quinones, for example dichlorodicyanoquinone.

It is also possible, however, for from 1 to 5 mol of an oxidising agent that acts simultaneously as halogenating agent to be added to the reaction mixture, the oxidation being carried out by halogenation and subsequent dehydrohalogenation. Preferred halogenating agents are chlorinating or brominating compounds, such as $Cl_2$, $Br_2$, sulfuryl chloride, N-haloimides, for example N-chloro- or N-bromo-succinimide or N-chloro- or N-bromo-phthalimide, or dihalodialkylhydantoins, for example dichlorodimethylhydantoin.

It is preferable to use from 1.2 to 4 mol and especially from 1.8 to 3 mol of oxidising agent or halogenating agent per mol of allyl isothiocyanate.

The oxidising agent or halogenating agent used is preferably a chlorinating or brominating compound and especially N-chloro- or N-bromo-succinimide, N-chloro- or N-bromo-phthalimide and dichlorodimethylhydantoin.

When a halogenating compound is used as oxidising agent, substitution takes place which, for example, is initiated or accelerated by UV light and/or by addition of a suitable initiator. Suitable initiators are customary compounds known from the prior art. They are, for example, peroxides, for example dibenzoyl peroxide, diacetyl peroxide, azo compounds, for example azobisisobutyronitrile, etc.

The initiator is used in an amount of from 0.05 to 10 mol %, preferably from 0.1 to 8 mol % and especially from 0.5 to 5 mol %, based on allyl isothiocyanate.

The oxidising agent and/or the initiator can be added either in one portion or divided into several portions.

The reaction temperature is from 0° C. to the boiling point of the solvent used. The reaction temperature is preferably from 20° C. to the boiling point of the solvent used and especially about from 30 to 80° C.

It is especially advantageous to the purity of the CCT when the reactions according to steps a) and b) are carried out under conditions that are as water-free as possible. This is achieved by the use of absolute solvents and pure allyl isothiocyanate, and if necessary by working under an inert gas atmosphere.

For the isolation and working-up of the CCT prepared, the reaction mixture is optionally first cooled.

When a N-haloimide is used as oxidising agent, precipitated imide is separated off, for example, optionally by filtration. The reaction mixture that remains behind is then rendered basic in order to bind any acids present, such as HCl or HBr. This can be carried out, for example, by washing with, or by adding, suitable bases. Suitable bases are, for example, $NaHCO_3$ solutions, $KHCO_3$ solutions, $Na_2CO_3$ solutions, $K_2CO_3$ solutions, dilute NaOH or KOH, aqueous ammonia, dry $Na_2CO_3$ or $K_2CO_3$ etc.

The solvent is then separated off and the crude CCT is purified, for example by simple distillation.

For further increasing the purity, the CCT-containing distillate can then be subjected to crystallisation and washing with, or digestion in, an aliphatic hydrocarbon, such as hexane, heptane etc., in an ether or ester. Aliphatic hydrocarbons are preferred.

Accordingly, in order to obtain high-purity CCT, the distillate (if necessary after separation of precipitated imide, basic washing, separation of the solvent and distillation) is preferably crystallised out by cooling to from 0 to −40° C., preferably to from −5 to −40° C. and especially to from −15 to −40° C., the crystals are filtered off with suction and digested while cold in an aliphatic, preferably ice-cold hydrocarbon, preferably in hexane or heptane, or in an ether or ester and then dried at room temperature in vacuo, if necessary under a nitrogen atmosphere.

During the crystallisation, the liquid above the crystals contains generally up to 29% by weight CCT, that is to say with CCT concentrations of 30% and more it is possible to obtain high-purity material from crude products of that kind.

By crystallisation it is possible, however, to increase the purity not only of distillates but also of solid commercially available CCT. For that purpose, the CCT to be purified is first dissolved in an aliphatic hydrocarbon, an ether or ester; active carbon is optionally added to the solution and any solids present are filtered off. Crystallisation and subsequent digestion are then carried out analogously to the above description.

The reaction procedure according to the invention yields CCT in substantially higher purities than in the prior art. As comparison experiments show, crude CCT prepared in accordance with the invention has scarcely any high molecular weight secondary products, as are the case, for example, with CCT prepared in accordance with EP 0 260 560.

Those high molecular weight secondary products cannot be identified or can be identified only with extreme difficulty by means of GC, but can be detected by means of HPLC-MS. By the working-up and purification according to the invention, CCT is obtained in substantially higher purities than in the prior art.

A further advantage of the process according to the invention is that it is performed in the form of a one-pot reaction which does not require complex apparatus.

EXAMPLE 1

29.7 g (0.22 mol) of sulfuryl chloride were added to 20 g (0.2 mol) of distilled allyl isothio-cyanate in 200 ml of dichloromethane at from −10 to −15° C. and the mixture was stirred for one hour at −15° C.

Then 53.36 g (0.4 mol) of N-chlorosuccinimide and 0.65 g (4 mmol) of azo-bis-isobutyronitrile were added and the mixture was heated at boiling under UV light for 3 hours.

The reaction mixture was cooled, precipitated succinimide was filtered off and the precipitate was washed twice using 5 to 10 ml of cooled dichloromethane each time.

The filtrates were washed twice with 50 ml of 5% $NaHCO_3$ solution each time, dried over sodium sulfate and the solvent was removed.

Yield analytically: 22.18 g of CCT (corresponds to 66% of theory)

(The quantitative gas-chromatographic analysis was always carried out with tetradecane as internal standard or using a derived method with an external standard.)

The crude product was purified by distillation at 60–65° C./2 mbar. A distillate having a CCT content of 85% was obtained.

Yield analytically: 17.75 g of CCT (52% of theory)

The distilled crude product was caused to crystallise by cooling to −20° C.; the crystals were filtered off with suction, digested twice with 5 ml of cold hexane each time and dried at room temperature in vacuo.

Yield: 13.8 g of colourless crystals having a CCT content of 99.8% (41% of theory)

EXAMPLE 2

6.7 g (50 mmol) of sulfuryl chloride were added in the course of 30 minutes to 4.9 g (50 mmol) of distilled allyl isothiocyanate in 60 ml of dichloromethane at −10° C. and the mixture was stirred for one hour at −10° C.

Then 13.3 g of N-chlorosuccinimide were added and the mixture was heated to boiling. A total of 240 mg (1.5 mmol) of azo-bis-isobutyronitrile in 4 ml of dichloromethane was then added in portions in the course of 3 hours and the mixture was heated for a further half an hour.

The reaction mixture was washed with 25 ml of sodium hydrogen carbonate solution and 20 ml of water, dried over sodium sulfate and filtered.

Yield analytically: 4.6 g of CCT (55% of theory)

The crude product was purified by distillation at 103–110° C./17 mbar. The distillate contained 74% by weight CCT.

Yield analytically: 4.0 g of CCT (48% of theory)

EXAMPLE 3

26.8 (0.2 mol) of sulfuryl chloride were added in the course of 75 minutes to 19.6 g (0.2 mol) of distilled allyl isothiocyanate in 240 ml of dichloromethane at −10° C. and the mixture was stirred for one hour at −10° C.

Then 26.6 g (0.2 mol) of N-chlorosuccinimide and 0.32 g (2 mmol) of azo-bis-isobutyronitrile in 8 ml of dichloromethane were added and the mixture was heated to boiling. There were then added three times at hourly intervals, on each occasion, 13.3 g (0.1 mol) of N-chlorosuccinimide and 0.32 g (2 mmol) of azo-bis-isobutyronitrile in 8 ml of dichloromethane and the mixture was finally heated at boiling for a further 2 hours.

Yield analytically: 21.7 g of CCT (64.5% of theory)

The reaction mixture was washed with 150 ml of saturated sodium hydrogen carbonate solution and three times with 100 ml of water each time, dried over sodium sulfate and the solvent was removed.

Yield analytically: 18.8 g of CCT (56% of theory)

EXAMPLE 4

14.8 (0.11 mol) of sulfuryl chloride were added in the course of 45 minutes to 9.9 g (0.1 mol) of distilled allyl isothiocyanate in 100 ml of dichloroethane at −10° C. and the mixture was stirred for one hour at −10° C.

Then 29.3 g (0.22 mol) of N-chlorosuccinimide and 0.32 g (2 mmol) of azo-bis-isobutyronitrile in 5 ml of dichloroethane were added and the mixture was heated at 70° C. for 2 hours.

The reaction mixture was cooled to −5° C. and the precipitated succinimide was filtered off.

Yield analytically: 9.46 g of CCT (56.3% of theory)

EXAMPLE 5

37.1 g (0.27 mol) of sulfuryl chloride were added in the course of 90 minutes to 24.8 g (0.25 mol) of distilled allyl isothiocyanate in 100 ml of dichloroethane at −10° C. and the mixture was stirred for one hour at −10° C.

Then 33.4 g (0.25 mol) of N-chlorosuccinimide and 0.82 g (5 mmol) of azo-bis-isobutyronitrile were added and the mixture was heated to 70° C. After ½ hour and after 1 hour, on each occasion a further 20.0 g (0.15 mol) of N-chlorosuccinimide and 0.41 g (2.5 mmol) of azo-bis-isobutyronitrile were added and the mixture was finally stirred for a further 2 hours at 70° C.

The reaction mixture was cooled to room temperature and the precipitated succinimide was filtered off.

Yield analytically: 16.8 g of CCT (40% of theory)

EXAMPLE 6

44.67 g (0.331 mol) of sulfuryl chloride were added in the course of 2 hours to 31.45 g (0.315 mol) of allyl isothiocyanate in 100 ml of dichloromethane at from −15 to −10° C. and the mixture was stirred for one hour at −10° C.

Then 42.02 g (0.315 mol) of N-chlorosuccinimide were added and the mixture was heated at boiling under UV light. After ½ hour and after a further hour, on each occasion a further 25.35 g (0.19 mol) of N-chlorosuccinimide were added and the mixture was finally heated for a further 2½ hours under UV light.

The reaction mixture was cooled to room temperature and the precipitated succinimide was filtered off.

Yield analytically: 25.4 g of CCT (48% of theory)

50.0 g (0.47 mol) of sodium carbonate were added to the crude product solution; the mixture was stirred for ½ hour at room temperature and filtered, and the solvent was removed.

Yield analytically: 24.94 g of CCT (47% of theory)

The crude product was purified by distillation at 66–70° C./3 mbar, distillates having a CCT content of 77% by weight being obtained.

Yield analytically: 36% of theory

EXAMPLE 7

7.8 g (0.11 mol) of chlorine were introduced in the course of 1 hour at from −15 to −10° C. into a solution of 10.91 g (0.11 mol) of allyl isothiocyanate in 100 ml of dichloromethane and the mixture was stirred for one hour at −10° C.

Then 22.03 g (0.165 mol) of N-chlorosuccinimide and 0.36 g (2.2 mmol) of azo-bis-isobutyronitrile were added and the mixture was heated to boiling. There were then added five times at ½ hourly intervals, on each occasion, 1.47 g (0.11 mmol) of N-chlorosuccinimide and 70 mg (0.44 mmol) of azo-bis-isobutyronitrile and the mixture was then heated at boiling for 10 hours.

The reaction mixture was cooled to 5° C. and the precipitated succinimide was filtered off.

Yield analytically: 10.54 g of CCT (57% of theory)

Comparison Example I (analogous to EP 0 260 560):

75 ml of chloroform at boiling temperature were saturated with chlorine. 25 g (250 mmol) of allyl isothiocyanate in 50 ml of chloroform were pumped into the solution in the course of 2 hours at boiling temperature and at the same time 133.7 g (1.91 mol) of chlorine gas were introduced, an excess of chlorine gas being constantly present. Then, in the course of a further ½ hour at boiling temperature, an additional 17.5 g (0.25 mol) of chlorine were introduced.

Excess chlorine was driven off with a stream of nitrogen and the yield was determined by means of GC analysis. The resulting solution (199.29 g) contained 6.99% by weight or 43% by area CCT. Yield analytically: 13.93 g of CCT (33% of theory)

Comparison Example II (analogous to EP 0 260 560)

75 ml of dichloromethane at boiling temperature were saturated with chlorine. 25 g (250 mmol) of allyl isothiocyanate in 50 ml of dichloromethane were pumped into the solution in the course of 1 hour at boiling temperature and at the same time 100 g (1.43 mol) of chlorine gas were introduced, an excess of chlorine gas being constantly present. Then, in the course of a further ½ hour at boiling temperature, an additional 85 g (1.21 mol) of chlorine were introduced.

Excess chlorine was driven off with a stream of nitrogen and the yield was determined by means of GC analysis. The resulting solution (80.02 g) contained 15.43% by weight or 38.8% by area CCT. Yield analytically: 12.35 g of CCT (29% of theory).

EXAMPLE 8

33.56 g of a crude distillate, prepared analogously to Example 2, having a CCT content of 70% by weight were caused to crystallise at −20° C. by the addition of seed crystals. The crystals were filtered off with suction and digested twice with a total of 25 ml of ice-cold hexane.

Yield: 15.08 g of colourless crystals; quality: 99.6% by weight CCT =64% of CCT used (mother liquor still contains 43% CCT)

EXAMPLE 9

12.20 g of a crude distillate containing 43.6% by weight CCT were caused to crystallise at −20° C. by the addition of seed crystals.

The crystals were filtered off with suction and then washed with 2 ml of ice-cooled hexane.

Yield: 2.23 g of colourless crystals; quality: 99.2% by weight CCT=42% of CCT used (mother liquor contains 27% CCT)

EXAMPLE 10

10.0 g of CCT (98.2% by weight CCT, Fine Organics) were dissolved at room temperature in 30 ml of hexane; 0.5 g of active carbon was added and the mixture was stirred for 15 minutes and then filtered. The mixture was then washed twice with a total of 4 ml of hexane and the filtrate was cooled to −20° C. The precipitated crystals were filtered off, digested while cold with 5 ml of hexane and dried in vacuo at room temperature.

Yield: 6.74 g of colourless crystals; quality: 101.3% by weight CCT

EXAMPLE 11

10.0 g of CCT (98.2% by weight CCT) were dissolved at 50° C. in 16 ml of hexane; the solution was then stirred for 15 minutes at room temperature, then filtered and the filtrate was cooled to −20° C. The precipitated crystals were filtered off, digested while cold with 2 ml of hexane and dried in vacuo at room temperature.

Yield: 9.06 g of colourless crystals; quality: 100.2% by weight CCT

What is claimed is:

1. A process for the preparation of 2-chloro-5-chloromethyl-1,3-thiazole, which is characterized in that
    (a) allyl isothiocyanate of the formula $CH_2=CH-CH_2-NCS$ is reacted at a temperature of from −40° C. to 30° C., in a solvent that is inert under the reaction conditions, optionally in an inert gas atmosphere, with from 1 to 2 mol of a chlorinating agent per mol of allyl isothiocyanate, said chlorinating agent being selected from the group, consisting of $Cl_2$, $SO_2Cl_2$, $PCl_3$, $PCl_5$ and $POCl_3$;
    (b) to the reaction mixture resulting from step (a), at a temperature of from 0° C. to the boiling temperature of the reaction mixture, from 1 to 5 mol of an oxidizing agent per mol of allyl isothiocyanate are added, said oxidizing agent being selected from the group, consisting of $Br_2$, an N-haloimide and a dihalodialkylhydantoin, optionally with the application of UV light and/or in the presence of a suitable initiator, optionally in an inert gas atmosphere; and
    (c) the 2-chloro-5-chloromethyl-1,3-thiazole is isolated from the reaction mixture resulting from step (b); and, if desired,
    (d) the isolated 2-chloro-5-chloromethyl-1,3-thiazole resulting from step (c) is converted by crystallization into high-purity 2-chloro-5-chloromethyl-1,3-thiazole.

2. A process according to claim 1, characterized in that the inert solvent is selected from the group, consisting of an aliphatic or aromatic hydrocarbon, which can be halogenated, an ether, a nitrile, an amide and a sulfoxide.

3. A process according to claim 1, characterized in that the chlorinating agent is chlorine or sulfuryl chloride.

4. A process according to claim 1, characterized in that the oxidizing agent is N-chloro- or N-bromo-succinimide or -phthalimide or dichlorodimethylhydantoin.

5. A process according to claim 4, characterized in that the oxidizing agent is N-chlorosuccinimide.

6. A process according to claim 1, characterized in that step (b) is carried out with the application of UV light and/or in the presence of a suitable initiator.

7. A process according to claim 1, characterized in that step (a) and step (b) are carried out under as water-free as possible conditions, using absolute solvents and pure allyl isothiocyanate, optionally in an inert gas atmosphere.

8. A process according to claim 1, characterized in that for the isolation of the 2-chloro-5-ohloromethyl-1,3-thiazole the reaction mixture resulting from step (b), which is optionally first cooled and freed from any precipitate, is rendered basic, the solvent is separated off, and the crude 2-chloro-5-chloromethyl-1,3-thiazole is purified by distillation.

9. A process according to claim 1, characterized in that in step (d) the isolated 2-chloro-5-chloromethyl-1,3-thiazole resulting from step (c) is crystallized out by cooling to a temperature of from 0° C. to −40° C., and the crystals are filtered off with suction, digested while cold in an aliphatic hydrocarbon, an ether or an ester and then dried.

* * * * *